United States Patent [19]

Busch, Jr.

[11] Patent Number: 4,839,163

[45] Date of Patent: * Jun. 13, 1989

[54] FACIAL COSMETIC LIQUID CONTAINING CRYSTALLINE SILICA AND COLORS

[75] Inventor: Francis Busch, Jr., Southbury, Conn.

[73] Assignee: Laura Lupton Inc., Rowayton, Conn.

[*] Notice: The portion of the term of this patent subsequent to Feb. 14, 2006 has been disclaimed.

[21] Appl. No.: 905,631

[22] Filed: Sep. 9, 1986

[51] Int. Cl.$^4$ ............................................. A61K 7/021
[52] U.S. Cl. ...................... 424/63; 514/770; 514/845; 514/951; 106/491
[58] Field of Search ................. 424/63, 127; 514/770, 514/844, 845, 847, 951; 106/482, 491

[56] References Cited

U.S. PATENT DOCUMENTS

| | | | |
|---|---|---|---|
| 3,639,572 | 2/1972 | Heinrich et al. | 424/63 |
| 4,119,712 | 10/1978 | Goldner et al. | 424/63 |
| 4,137,302 | 1/1979 | Humbert et al. | 424/63 |

FOREIGN PATENT DOCUMENTS 228406 10/1985 Japan ..................................... 424/63

*Primary Examiner*—Ellis P. Robinson
*Assistant Examiner*—Susan S. Rucker

[57] ABSTRACT

A facial cosmetic liquid contains a coloring phase containing crystalline mineral silica and coloring material; a major water phase containing water, an emulsifying component and a thickening component; and a minor oil phase containing emolient oils and an emulsifying component.

7 Claims, No Drawings

FACIAL COSMETIC LIQUID CONTAINING CRYSTALLINE SILICA AND COLORS

CROSS REFERENCE TO COPENDING APPLICATION

The present application is related to copending application entitled FACIAL COSMETIC POWDER CONTAINING CRYSTALLINE SILICA AND COLORS, Ser. No. 905,630 filed on even date herewith and owned by the assignee of the present application.

THE PRIOR ART

Certain foundation cosmetic creams are now described and sold as wrinkle smoothers and pore minimizers. One such cream employs 25-40 parts by weight of crystalline silica. This mineral is employed because the cream is totally transparent and the refractive index and plate-like shape of the mineral permits the cream as applied to be indistinguishable from the skin itself, making lines and pores difficult to see. However, it is a characteristic of this cream that, when in place and viewed directly at an angle of ninety degrees, the wrinkles, lines and pores which lie underneath the foundation become visible. The silica itself is sold commercially by Malvern Minerals Company of Hot Springs National Park, Ark. under the brand name 1250 NOVACITE. It has an average particle size falling within the range of 7.3 to 12.9 microns and the particles have a characteristic plate like shape.

SUMMARY OF THE INVENTION

The present invention is directed toward a facial cosmetic liquid utilizing crystalline silica in substantially smaller parts [2-10] by weight. The function of liquid makeup is to impart a smooth finish to the skin which masks or covers variations of skin color, blemishes on the skin, freckles or dark spots. To this end, the liquid must contain significant amounts of coloring material. In the present invention, the use of the silica enables the liquid to contain a larger amount of coloring material than previously obtainable, thus obtaining a much wider range of color and shade of coating, without causing the coating to appear chalky or caked on the skin.

In accordance with the principles of the invention, the facial cosmetic liquid is composed of a color phase, a water phase and an oil phase. The color phase is produced in powder form. The water and oil phases are produced separately and combined as a water-oil emulsion and the color phase is mixed into the emulsion to produce the final cosmetic liquid. The water phase is a major and much larger phase in the emulsion while the oil phase is a minor and much smaller phases in the emulsion. The emulsion could take the form of an oil-water emulsion consisting of a major oil phase and a minor water phase, but for health reasons, the oil content is minimized.

The color phase contains titanium dioxide, one or more iron oxide colors, and crystalline silica. These constituents are then processed through a high shear dispersion machine such as a hammer mill. The processing is continued until the colors are coated onto the silica which has a flat plate-like shape.

The water phase contains water, an emulsifying component, and a thickening component. As is customary, this phase also includes various trace ingredients. These constituents are heated with moderate mixing until their temperature is raised from room temperature to seventy five degrees Centigrade.

The oil phase contains one or more emolient oils, and an emulsifying component. As is customary, this phase also includes trace ingredients. These constituents are processed in the same manner as the constituents in the water phase.

The water and oil phases so produced are combined with moderate mixing to produce the desired emulsion. Then the color phase is added and blended into the emulsion with moderate mixing until the smooth finished product is obtained.

The final product, the facial cosmetic liquid contains 2-10 parts by weight of the crystalline silica; 3-12 parts by weight of iron oxide coloring material; 4-10 parts by weight of titanium dioxide; 45-65 parts by weight of water; 4-7 parts by weight of emulsifing components; 0.2-1.5 parts by weight of a thickening component; 4.5-5.5 parts by weight of emolient oils; and known trace ingredients.

Different colors such as gold, peach, rose and blush are obtained in known manner by mixing together different proportions of iron oxide materials identified in the trade as russet, brown, yellow, red and ultramarine blue.

The plate-like structure of the crystalline silica enables it to become a carrier of the coloring material which adheres thereto. The amount of coloring material suspended uniformly in a given weight of powder when the silica is used is substantially increased as compared to the amount of coloring material suspended uniformly in the same weight of powder when the conventional technique of using talc as the color carrier is used. As a result, the covering power of the powders in accordance with the invention is substantially increased in the resultant product whereby the facial wrinkles, lines and pores of the user can be completely hidden when this facial cosmetic liquid is used and, at the same time, the coating does not have a chalky or caked appearance on the skin.

The emulsifying components used in the different oil and water phases are materials known in the art to be necessary to insure formation of an acceptable emulsion. Similarly, the trace ingredients are materials known in the art to be necessary in producing acceptable facial cosmetic liquids.

SPECIFIC EXAMPLE

A typical facial cosmetic liquid in accordance with this invention has the following formula:

| INGREDIENT | PARTS BY WEIGHT |
| --- | --- |
| color phase constitents | |
| titanium dioxide | 8.235 |
| yellow iron oxide | 0.529 |
| brown iron oxide | 0.471 |
| red iron oxide | 0.235 |
| crystalline silica | 8.0 |
| water phase constituents | |
| propylene glycol | 4.00 |
| water | 60.215 |
| glycerin | 3.00 |
| carbomer 934 [2% concentration] | 2.75 |
| [carbomer is a thickening component] | |
| methylparaben | 0.09 |
| disodium EDTA | 0.03 |
| aluminum magnesium silicate | 0.12 |
| [this silicate is a thickening component] | |
| triethanol amine | 0.92 |

-continued

| INGREDIENT | PARTS BY WEIGHT |
|---|---|
| [this amine is an emulsifying component] | |
| oil phase constituents | |
| mineral oil [an emolient oil] | 3.34 |
| glycol stearate | 1.37 |
| [glycol stearate is an emulsifying component] | |
| stearic acid | 2.30 |
| [stearic acid is an emulsifying component] | |
| acetylated lanolyn alcohol | 0.60 |
| cetyl alcohol | 0.18 |
| silicone oil | 0.50 |
| propyl paraben | 0.06 |

What is claimed is:

1. A facial cosmetic liquid which when applied to the face of a user completely hides facial wrinkles, lines and pores without caking or appearing chalky, said liquid comprising:

a coloring phase containing crystalline mineral silica and coloring material, said silica having a plate-like structure and an average particle size falling within the range of 7.3 to 12.9 microns, the silica content falling within the range of 1–10 parts by weight of liquid;

a major water phase containing water, an emulsifying component and a thickening component; and a minor oil phase containing emollient oils and emulsifying component.

2. The liquid of claim 1 containing between 45 and 65 parts per weight of water.

3. The liquid of claim 2 containing between 4.5 to 5.5 parts per weight of emollient oils.

4. The liquid of claim 3 containing between 3 to 12 parts by weight of iron oxide coloring material.

5. The liquid of claim 4 containing between 4 to 10 parts by weight of titanium dioxide.

6. The liquid of claim 5 containing 4 to 7 parts by weight of emulsifing components.

7. The liquid of claim 6 containing 0.2 to 1.5 parts by weight of thickening components.

* * * * *